United States Patent [19]
Bergstrom

[11] Patent Number: 5,988,180
[45] Date of Patent: *Nov. 23, 1999

[54] LEAVE-ON OXIDIZING SOLUTION FOR PERMANENT WAVING OF HAIR AND A PROCESS FOR PERMANENT WAVING OF HAIR

[75] Inventor: Joan M. Bergstrom, Fridley, Minn.

[73] Assignee: Zotos International, Inc., Darien, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/815,695

[22] Filed: Mar. 12, 1997

Related U.S. Application Data

[63] Continuation of application No. 08/725,062, Oct. 2, 1996, abandoned, which is a continuation of application No. 08/362,697, Dec. 22, 1994, abandoned.

[51] Int. Cl.$^6$ ........................... A45D 7/04
[52] U.S. Cl. ................. 132/204; 132/202; 132/203; 424/70.2
[58] Field of Search .................. 424/70.2, 70.4; 132/203, 204, 202

[56] References Cited

U.S. PATENT DOCUMENTS

| | | | |
|---|---|---|---|
| 2,983,569 | 5/1961 | Charle et al. | 8/127.5 |
| 3,459,198 | 8/1969 | Zemlin et al. | 132/7 |
| 3,768,490 | 10/1973 | Kalopissis et al. | 132/7 |
| 3,913,593 | 10/1975 | Sato | 132/251 |
| 4,134,411 | 1/1979 | Yamazaki | 132/7 |
| 4,192,863 | 3/1980 | Kondo | 424/72 |
| 4,201,235 | 5/1980 | Ciavatta | 132/7 |
| 4,349,537 | 9/1982 | Forbriger, Jr. | 424/70.2 |
| 4,366,827 | 1/1983 | Madrange et al. | 132/7 |
| 4,416,297 | 11/1983 | Wolfram et al. | 132/7 |
| 4,660,580 | 4/1987 | Hoch et al. | 132/7 |
| 4,770,872 | 9/1988 | Hsiung et al. | 424/71 |
| 4,793,994 | 12/1988 | Helioff et al. | 424/71 |
| 4,798,722 | 1/1989 | Edman et al. | 424/72 |
| 4,919,924 | 4/1990 | Pigiet | 424/72 |
| 4,935,230 | 6/1990 | Naito et al. | 424/70 |
| 4,935,231 | 6/1990 | Pigiet | 424/71 |
| 4,941,885 | 7/1990 | Pigiet | 8/161 |
| 5,051,252 | 9/1991 | Schultz et al. | 424/71 |
| 5,080,890 | 1/1992 | Ueno | 424/71 |
| 5,165,427 | 11/1992 | Borish | 132/204 |
| 5,260,054 | 11/1993 | Nandagiri et al. | 424/71 |
| 5,277,206 | 1/1994 | Rose et al. | 132/204 |
| 5,293,885 | 3/1994 | Darkwa et al. | 132/203 |
| 5,294,230 | 3/1994 | Wu et al. | 132/203 |
| 5,332,570 | 7/1994 | Bergstrom et al. | 424/72 |
| 5,520,909 | 5/1996 | Salce et al. | 424/70.51 |
| 5,715,845 | 2/1998 | Samain | 132/204 |
| 5,775,342 | 7/1998 | Hohenstein et al. | 132/204 |

FOREIGN PATENT DOCUMENTS

| | | |
|---|---|---|
| 80922/87 | of 1990 | Australia. |
| 0 257 256 | of 1988 | European Pat. Off.. |
| 36 10 394 A1 | of 1987 | Germany. |
| 42 10 481 A1 | of 1993 | Germany. |
| 54-113446 | of 1979 | Japan. |

OTHER PUBLICATIONS

Japanese Public Patent Disclosure Bulletin No.: 48–38859, Jun. 7, 1973, Ito et al.
Japanese Public Patent Disclosure Bulletin No.: 51–15639, Feb. 7, 1976, Takehara et al.
Japanese Public Patent Disclosure Bulletin No.: 54–86635, Jul. 10, 1979, Hiroshi Isokuni.
Abstract, Derwent Publications Ltd., J54113446–A, Assignee Saka/Sakai Y, Sep. 5, 1979.
Abstract, J57179–110, Lion Corporation, Apr. 25, 1981.
Abstract, Derwent Publications Ltd., J6 0120–807–A, Jan. 12, 1983, Lion Corporation.
Japanese Public Patent Disclosure Bulletin No.: 60–197615, Susumu Morita, Oct. 1, 1985.
Abstract, Derwent Publications Ltd., DE 3610394–A, Hartmann et al., Oct. 1, 1987.
62–Essential Oils, Cosmetics, vol. 103, p. 319, 103:11226z Permanent wave neutralizer containing aluminum and/or zirconium compounds and hair cold waving, 1985.
Abstract, Derwent Publications Ltd., DE4210481–A1, Glauder et al., Oct. 7, 1993.
LaMaur, Something Right For Your Hair, 5 pages.

*Primary Examiner*—Robert H. Harrison
*Attorney, Agent, or Firm*—Moore & Hansen

[57] ABSTRACT

A leave-on oxidizing solution useful for permanent waving of hair containing water, an oxidant which is capable of being left on the hair and dried on the hair without damage to the hair, and an acidic agent to provide the solution with a pH value of less than about 7. The use of the leave-on oxidizing solution decreases the amount of time required for carrying out a permanent waving of hair process.

9 Claims, No Drawings

LEAVE-ON OXIDIZING SOLUTION FOR PERMANENT WAVING OF HAIR AND A PROCESS FOR PERMANENT WAVING OF HAIR

"This is a continuation of application Ser. No. 08/725,062 filed Oct. 2, 1996, which is a continuation of application Ser. No. 08/362,697 filed Dec. 22, 1994 both now abandoned."

BACKGROUND OF THE INVENTION

This invention relates to a "leave-on" oxidizing solution for use in the permanent waving ("permiting") of hair and to a process for permanent waving of hair.

Generally, permanent waving of human hair involves a reducing step and an oxidation step. The reducing step involves application of a reducing solution to hair to chemically break sulfur to sulfur or disulfide cystine bonds occurring naturally in human hair. The disulfide cystine bonds in human hair maintain the hair shape or configuration. While the disulfide cystine bonds are broken, the hair can be rearranged into a different configuration. The oxidation step involves application of a neutralizing solution to restore the disulfide bonds in the new rearranged configuration.

A reducing agent in the reducing solution chemically breaks the disulfide bonds in the hair. Examples of reducing agents useful in reducing solutions include cysteamine, esters and salts of thioglycolic acid, cysteine and thiolactic acid. Typical examples of reducing agents and conventional reducing solutions are taught in U.S. Pat. Nos. 5,260,054 and 5,332,570.

An oxidizing agent in the neutralizing solution reform the disulfide bonds in their new "curled" formations. Examples of oxidizing agents useful in neutralizing solutions include bromic acid salts, perboric acid and hydrogen peroxide. Typical examples of oxidizing agents and conventional neutralizing solutions are taught in U.S. Pat. Nos. 5,277,206; 5,080,890 and 5,051,252.

In traditional permanent waves a conventional neutralizing solution used to rebond keratin disulfides, applied after reduction to rolled hair, is left on the hair for only about five minutes and then is thoroughly rinsed off the hair. It is well known that if a conventional neutralizing solution is left on the hair, it can cause damage to the hair. Damage to the hair is qualitatively seen as hair color lightening; damage to hair is quantitatively seen as an increased amount of cysteic acid. The rinsing of the conventional neutralizing solution off the hair is critical to keep hair damage to a minimum. It would be desirable to provide a new oxidizing solution which can be applied after a reduction step to rolled or unrolled hair and left on the hair without having to rinse the oxidizing solution from the hair and without the oxidizing solution causing damage to the hair.

Under normal circumstances, traditional perms may take from 1 ½ to 3 hours and follow a strict standard procedure. The process steps of the known permanent wave process include for example:

(1) shampooing hair for about 5 minutes;
(2) wrapping the hair on rods which takes about 30 to 90 minutes;
(3) applying a reducing solution on the wrapped hair and processing for 20 to 40 minutes;
(4) rinsing off the reducing solution for about 5 minutes:
(5) blotting water from the hair on the rods for about 3 to 5 minutes;
(6) applying a neutralizing solution to the hair on the rods and waiting about 5 minutes;
(7) rinsing off the neutralizing solution from the hair for about 5 minutes; and
(8) removing the rods from the hair and styling the hair for about 10 to 30 minutes.

It would be desirable and economically advantageous to a stylist to use a permanent wave process that allows the stylist to complete a permanent wave service with identical curl results as traditional perms in significantly less time. Of course, the more clients a stylist can see in a day, the more money the stylist can make. Thus, there is an incentive for those in the art to continuously seek improvement to the permanent wave process.

SUMMARY OF THE INVENTION

The present invention involves a novel leave-on oxidizing solution containing an oxidant that is useful in the permanent waving of hair. In use, the oxidizing solution of the present invention is left on the hair and is dried on the hair. The use of the oxidizing solution of the present invention results in perm curls comparable to curls obtainable with traditional perms without increasing damage to hair.

In accordance with the present invention, an oxidizing solution that can remain on hair without hair color lightening or dry hair feel as a result of perming hair is provided. The present invention includes the discovery that the use of lower amounts of an oxidant in oxidizing solutions used in permanent waving of hair results in permed hair without the hair damage over hair permed using oxidizing solutions containing greater amounts of oxidants. For example, in one embodiment of the present invention, less than about 40 percent of a standard amount of oxidizing agent is used; and by utilizing less than 40 percent of the standard amount of oxidizing agent in an aqueous solution, the oxidizing solution when dried on the hair provides almost no hair color lightening and minimal cysteic acid production within the hair.

Also a time savings advantage as well as physical discomfort reduction over the traditional permanent wave procedure is obtained with use of the oxidizing solution of the present invention.

One aspect of the present invention is directed to an aqueous leave-on oxidizing solution useful in permanent waving of hair, comprising a functional amount of oxidant to provide oxidation of hair with minimal damage to hair; a sufficient amount of an acidic agent to adjust the pH of the oxidizing solution to a pH of less than about 7; and water.

Another aspect of the present invention is directed to a process for permanent waving of hair including the steps of applying a reducing solution on the hair; applying an oxidizing solution on the hair; and drying the hair with the oxidizing solution remaining on the hair.

DESCRIPTION OF THE PREFERRED EMBODIMENTS

The novel composition of the present invention comprises an aqueous leave-on oxidizing solution containing an oxidant as an essential ingredient in an amount sufficient to provide the required oxidation to hair without the unwanted damage to hair. By "leave-on" it is meant that the oxidizing solution of the present invention is evenly applied to the hair and the hair is dried without an intermediate step of rinsing the oxidizing solution off the hair. The present invention provides the advantage of speed and ease of use.

Generally, the oxidizing solution of the present invention contains a functional amount of oxidizing agent. A functional amount of oxidizing agent is any amount that allows the oxidizing solution to be used effectively in the permanent waving of human hair and left on the hair without causing substantial damage to the hair. The functional amount of oxidizing agent may vary depending on the type of oxidizing agent used.

The amount of oxidant used in the solution of the present invention is sufficient to provide the solution with a preferred concentration of available oxygen. Preferably, the oxidizing solution of the present invention contains a concentration of less than about 2 percent by weight of available oxygen in solution. More preferably, the oxidizing solution of the present invention contains a concentration of from about 0.5 percent by weight to about 1.5 percent by weight of available oxygen in the solution. Most preferably, the oxidizing solution of the present invention contains from about 1 percent by weight to about 1.2 percent by weight of available oxygen.

Treating hair with oxidizing solutions of the present invention containing a low concentration of available oxygen provides less damage to the hair than treating hair with conventional oxidizing solutions containing a high concentration of available oxygen. Thus, increasing the concentration of available oxygen above about 2 percent in the oxidizing solution of the present invention results in increased hair damage such as hair color lightening. Lowering the concentration of available oxygen below about 0.5 percent in the oxidizing solution results in an oxidizing solution that will not impart sufficient hair curl efficiency and/or curl durability.

The oxidant used in the oxidizing solution of the present invention may be any material which is known as an oxygen donor or provides the required concentration of available oxygen in the oxidizing solution. The oxidant used in the oxidizing solution of the present invention may be, for example, peroxide materials such as hydrogen peroxide and organic peroxides such urea peroxide and the alkali metal and ammoniated salts of bromide, persulfate and carbonates. Examples of oxidants useful in the present invention include alkali metal perborates such as sodium perborate; alkali metal percarbonates such as sodium percarbonate; and alkali metal bromates such as sodium bromate. Other oxidants include, for example, potassium bromate, potassium perborate, sodium iodate and sodium periodate. Preferably, the oxidant used in the oxidizing solution is sodium perborate because it gives a crisp feel to hair which is aesthetically pleasing to consumers. In addition, it has been surprisingly discoverd that an oxidant such as sodium perborate used in an aqueous solution is stable at the preferred pH range and concentration range of available oxygen. By "stable" it is meant that the available concentration of oxygen does not decrease over time, for example, from about 3 months to about 1 year. This discovery is contrary to what is known in the art that an oxidant such as sodium perborate loses its available oxygen concentration within 1 week when used in an aqueous oxidizing solution.

Generally, the oxidizing solution of the present invention contains a sufficient amount of acidic agent as an essential ingredient to provide the oxidizing solution with the necessary pH for stabilization of the oxidant in solution, for causing de-swelling of hair and for restoring the disulfide bonds in the hair. Preferably, the pH of the oxidizing solution is below about 7, more preferably from about 2 to about 6, and most preferably from about 3 to about 5. The higher the pH the less salt is formed in situ and the lower the pH, the more salt is formed which tends to interfere with and decrease the amount of bond reformation. The salt formed can be, for example, sodium phosphate when using phosphoric acid and sodium perborate. Achieving a desired pH may also depend on the oxidant used in the oxidizing solution.

The amount of acidic agent used in the oxidizing solution of the present invention is generally from about 0.01 percent by weight to about 10 percent by weight, preferably from about 0.05 percent to about 5 percent. There is no advantage in using an amount above about 10 percent of acidic agent to effect a pH change and the use of an acidic agent in amounts below about 0.01 percert may not provide the necessary pH. Also, using amounts of acidic agent outside the above ranges may result in an oxidizing solution which is less stable and less effective.

The acidic agent used in the oxidizing solution of the present invention may be, for example, phosphoric acid, hydrochloric acid, citric acid, and other conventional acids useful for providing the desired pH to the oxidizing solution. Preferably, phosphoric acid is used in the oxidizing solution because the use of a small amount of phosphoric acid achieves a large pH change.

An ingredient preferably used in the oxidizing solution of the present invention includes a chelating agent. Since extraneous metals which may be present in the oxidizing solution can cause decomposition of the oxidant, a small amount of a chelating agent is preferably used to assure stability of the oxidant in the oxidizing solution. The chelating agent is preferably in solution before the oxidant is added to the solution to ensure that decomposition of the oxidant does not occur.

The amount of chelating agent used in the present oxidizing solution may be from about 0.01 percent to about 0.5 percent by weight, preferably from about 0.05 percent to about 3 percent and more preferably from about 0.1 percent to about 2 percent. Less than about 0.01 percent of chelating agent used in the oxidizing solution is ineffective and above about 0.5 percent is not necessary and interferes with the oxidation reaction.

The chelating agent used in the composition of the present invention can be selected from any salt of ethylene diamine tetraacetic acid (EDTA); phosphonates; and pentasodium pentatate such as Versenex (Trademark of The Dow Chemical Company) 80 commercially available from The Dow Chemical Company. Preferably, pentasodium pentatate is used in the oxidizing solution because it is active, in the preferred pH range, in chelating specific prevalent metals present in solution such as iron, magnesium and calcium which may react with the preferred oxidants.

Other optional ingredients may be added to the oxidizing solution of the present invention including, for example, surfactants; hair grooming agents; dyes; perfume oils; conditioning agents, for example, the polymeric quaternary ammonium salts and compounds listed in U.S. Pat. No. 5,165,427 incorporated by reference, and preferably, polyquaternium-7 such as Merquat 550 commercially available from Merck & Co., Inc. or acetamidopropyl trimonium chloride such as Incromectant AQ commercially available from Croda, Inc.; UV absorbers; resin or holding polymers; thickeners; emulsifying agents; and fragrances for example laureth-23 such as Brij 35 commercially available from ICI United States, Inc. The optional additional ingredients are used in the oxidizing solution, for example, to provide hair with better feel or styling properties; or to facilitate solubilizing other ingredients. Any other ingredients may be used which will not detrimentally affect the function of the oxidant or other essential ingredients in the oxidizing solution of the present invention.

The amount of these non-essential additives used in the oxidizing solution may be from about 0.01 to about 30 percent, preferably from about 0.1 to about 20 percent, more preferably from about 0.5 percent to about 10 percent by weight of the oxidizing solution. The use of too many or too much (above about 30 percent) of additional ingredients can provide aesthetically unappealing attributes to the hair and can inhibit the occurrence of oxidation in the hair. The use of less than about 0.01 percent of additional ingredients may add no benefit to the oxidizing solution.

The method of making the oxidizing solution of the present invention generally involves mixing together the essential and optional ingredients. If any of the ingredients are in solid form such as the surfactant used, the solids are melted first, and then, the other ingredients such as the fragrance is added to the melted solids before mixing the solids with a premix of the remaining ingredients. An acidic agent is added to the mixture adjust the pH to the desired range.

Broadly, the process of using the composition of the present invention involves a process for perming hair and applying a leave-on oxidizing solution useful in permanent waving of hair comprising the steps of applying a reducing solution on the hair; thereafter applying an oxidizing solution to the hair; and then drying the hair without rinsing off the oxidizing solution from the hair, i.e., leaving the oxidizing solution on the hair. Advantageously, by leaving the oxidizing solution on the hair and drying the oxidizing solution on the hair, shampooing of the dried hair can take place at any time thereafter (in as little as a few minutes) unlike in a traditional permanet waving of hair procedure wherein the hair can only be shampooed after at least 24 hours and preferably after 48 hours to ensure the durability of the permanent wave.

As an illustration of one embodiment of the permanent waving process of the present invention, the specific steps of the process may include, for example, a first step of shampooing the hair. After shampooing the hair which is an optional step, some means for providing the hair with mechanical tension or mechanical deformation is applied to the hair. For example, the hair may be wrapped with at least one rod or roller of suitable shape and dimensions; the hair may be clamped with clips; the hair may be wrapped with aluminum foil; the hair may be held with rope or tied; or the hair may be straightened with combing.

After applying a mechanical tension to the hair or straightening the hair, a reducing solution is applied on the hair, for example, a reducing solution described in U.S. Pat. No. 5,332,570 incorporated herein by reference. The hair with reducing solution is processed for 10 to 30 minutes at room temperature or for a shorter period of time at a temperature of 40° C. to 50° C. (hair dryer temperature).

The reducing solution is then rinsed off from the hair. After the reducing solution is removed from the hair, an oxidizing solution is applied to the hair, preferably at room temperature (about 23° C.). The mechanical tensioning means as used in the step described above can be removed from the hair before or after the step of applying the oxidizing solution. This step of applying the oxidizing solution takes usually less than 2 minutes.

The final step in the preferred process of the present invention is drying the hair with the oxidizing solution remaining on the hair. The process of the present invention can be used for both adding curl to hair or removing curl from hair.

The following examples further illustrate the preferred embodiments within the scope of the present invention. The examples are given solely for the purposes of the illustration and are not construed as limitation of the present invention as many variations of the invention are possible without departing from its spirit and scope. The stated amounts are in weight percents unless indicated otherwise.

EXAMPLE 1

An oxidizing solution of the following composition is applied to a tress of hair which has been treated with a conventional mild-alkaline reducing solution based on ammonium thioglycolate:

| Ingredient | % by weight |
| --- | --- |
| Sodium perborate (15% by weight available $O_2$) | 4.50 |
| Pentasodium pentatate | 0.10 |
| Phosphoric acid for adjustment to pH 3.0 | q.s. |
| Deionized water ad | ad 100 |

The above oxidizing solution is left on the hair and the hair dried. A shiny, well-waved tress is obtained.

EXAMPLE 2

An oxidizing solution of the following composition is applied to a tress of hair which has been treated with a conventional mild-alkaline reducing solution based on ammonium thioglycolate:

| Ingredient | % by weight |
| --- | --- |
| Sodium perborate (15% by weight available O$_2$) | 4.50 |
| Pentasodium pentatate | 0.10 |
| Phosphoric acid to pH 5.0 | q.s. |
| Deionized water ad | ad 100 |

The above oxidizing solution is not rinsed from the hair. Instead, the oxidizing solution is left on the hair and is dried on the hair. A shiny, well-waved tress is obtained.

EXAMPLE 3

An oxidizing solution of the following composition is applied to a tress of hair which has been treated with a mild-alkaline reducing solution based on cysteamine:

| Ingredient | % by weight |
| --- | --- |
| Sodium perborate (15% by weight available O$_2$) | 4.50 |
| Pentasodium pentatate | 0.10 |
| Phosphoric acid to pH 3 | q.s. |
| Deionized water ad | ad 100 |

The above oxidizing solution is left on the hair and the hair dried. A shiny, well-waved tress is obtained.

EXAMPLE 4

An oxidizing solution of the following composition is applied to a tress of hair which has been treated with a mild-alkaline perm solution based on cysteamine:

| Ingredient | % by weight |
| --- | --- |
| Sodium perborate (15% by weight available O$_2$) | 4.50 |
| Pentasodium pentatate | 0.10 |
| Phosphoric acid to pH 5.0 | q.s. |
| Deionized water ad | ad 100 |

The above oxidizing solution is left on the hair and the hair dried. A shiny, well-waved tress is obtained.

EXAMPLE 5

An oxidizing solution of the following composition is applied to a tress of hair which has been treated with a conventional mild-alkaline reducing solution based on ammonium thioglycolate:

| Ingredient | % by weight |
| --- | --- |
| Hydrogen peroxide (35% available oxygen) | 5.71 |
| Pentasodium pentatate | 0.10 |
| Phosphoric acid to pH 3.0 | q.s. |
| Deionized water ad | ad 100 |

The above oxidizing solution is left on the hair and the hair is dried. A shiny, well-waved tress is obtained.

EXAMPLE 6

An oxidizing solution of the following composition is applied to a tress of hair which has been treated with a conventional mild-alkaline reducing solution based on ammonium thioglycolate:

| Ingredient | % by weight |
| --- | --- |
| Hydrogen peroxide (35% available oxygen) | 5.71 |
| Pentasodium pentatate | 0.10 |
| Phosphoric acid to pH 5.0 | q.s. |
| Deionized water ad | ad 100 |

The above oxidizing solution is left on the hair and the hair is dried. A shiny, well-waved tress is obtained.

EXAMPLE 7

An oxidizing solution of the following composition is applied to a tress of hair which has been treated with a mild-alkaline reducing solution based on cysteamine:

| Ingredient | % by weight |
| --- | --- |
| Hydrogen peroxide (35% available oxygen) | 5.71 |
| Pentasodium pentatate | 0.10 |
| Phosphoric acid to pH 3.0 | q.s. |
| Deionized water ad | ad 100 |

The above oxidizing solution is left on the hair and the hair is dried. A shiny, well-waved tress is obtained.

EXAMPLE 8

An oxidizing solution of the following composition is applied to a tress of hair which has been treated with a mild-alkaline reducing solution based on cysteamine:

| Ingredient | % by weight |
| --- | --- |
| Hydrogen peroxide (35% available oxygen) | 5.71 |
| Pentasodium pentatate | 0.10 |
| Phosphoric acid to pH 5.0 | q.s. |
| Deionized water ad | ad 100 |

The above oxidizing solution is left on the hair and the hair is dried. A shiny, well-waved tress is obtained.

EXAMPLE 9

The oxidizing solutions of Examples 1–8 were used in a series of studies conducted to determine the curl efficiency and durability of the curl obtained from using the oxidizing solution and permanent waving procedure of the present invention. The general procedures used in this example are described below and the results are shown in Table I below.

Waving Efficiency Procedure and Measurement

The permanent waving efficiency of the oxidizing solution is measured by a modified peg board method similar to the methods known in the art. A predetermined length of the tresses is wound with even tension around the pegs arranged in a zig-zag pattern and treated with a reducing solution. After a period of exposure to the reducing solution, the hair is rinsed and an oxidizing solution applied and left on. The wet hair is removed from the pegs and the length of a portion of the waved tress is compared with the length of a similar portion of the rows of the pegs. Hair length is measured in centimeters (cm). Efficiency is indicated as a percentage based on the increased length of the waved wet tress as compared with the distance between the respective pegs. An efficiency of 100 percent represents hair that did not change dimension upon removal from the pegs. Generally, an efficiency in the range of about 60 percent to about 85 percent is desired.

The efficiency is measured as follows:

About 0.5 gram hair tresses, each tress being 20 cm long, are used for measuring the waving efficiency of the permanent wave. About 14.7 cm length of hair are wound with even tension, between points A and B about 4 cms apart (about 6 wave lengths), around the pegs arranged in a zig-zag pattern on a wave board similar to the peg boards known in the art. Wrapped peg boards are submerged for approximately five seconds at room temperature (about 23° C.) in the reducing solution. The boards are then placed inside ZIPLOC® bags at room temperature for 20 minutes. Each peg board is then rinsed thoroughly with warm water for about five minutes. The peg boards are blotted and an oxidizing solution is applied and left on the tress. The tresses are removed from the peg boards and the "wet" lengths of the tresses measured and recorded. The curl efficiency is calculated from the equation below:

$$1 - \frac{(x-4)}{(14.7-4)} \times 100 = y$$

where x is the permed wet hair length (cm) between the two points A and B, and y is the perm efficiency (%).

The permed hair tress can attain a maximum curl of 4 cms resulting in 100 percent efficiency or the tress may measure 14.7 cm in length resulting in no curl and 0 percent perm efficiency.

Durability Test Method

The durability of the curl is determined by shampooing the curled tresses. The tresses are held in a palm of the hand and about 1 milliliter of shampoo is placed in the palm holding the tress. A lather is built up by rubbing the tresses with the shampoo with the palm of the other hand, with both hands working in an opposite circular motion with respect to each other. The tresses are then rinsed in water at 100° C. for about 20 seconds and blotted. The length of the curled tress is then measured to determine the change in the curl. The shampoo, the rinse, and the measurement steps are repeated five times to determine the duration of the curl after 5 shampoos respectively. The smaller the tress length difference after the 5 shampoos, the more durable is the curl.

TABLE I

| Composition | Initial Wet Tress Length (cm) | Waving Efficiency of Curl (%) | Initial Dry Tress Length (cm) | Dry Tress Length After Five Shampoos (cm) | Durability of Curl: Tress Length Difference (cm) |
| --- | --- | --- | --- | --- | --- |
| Example 1 | 6.2 | 79.4 | 6.2 | 7.4 | 1.2 |
| Example 2 | 6.4 | 77.6 | 5.7 | 6.7 | 1.0 |
| Example 3 | 7.5 | 67.3 | 8.0 | 8.6 | 0.6 |
| Example 4 | 7.4 | 68.2 | 7.9 | 8.5 | 0.6 |

TABLE I-continued

| Composition | Initial Wet Tress Length (cm) | Waving Efficiency of Curl (%) | Initial Dry Tress Length (cm) | Dry Tress Length After Five Shampoos (cm) | Durability of Curl: Tress Length Difference (cm) |
| --- | --- | --- | --- | --- | --- |
| Example 5 | 6.2 | 79.4 | 5.8 | 7.0 | 1.2 |
| Example 6 | 6.3 | 78.5 | 6.4 | 6.9 | 0.5 |
| Example 7 | 7.4 | 68.2 | 7.5 | 8.2 | 0.7 |
| Example 8 | 7.2 | 70.1 | 7.2 | 8.3 | 1.1 |

EXAMPLE 10

Table II shows the composition of one example of an embodiment of the present invention ("Example 10") as well as a comparative sample ("Conventional Neutralizing Solution").

TABLE II

| | Percent by Weight | |
| --- | --- | --- |
| Ingredient | Example 10 | Conventional Neutralizing Solution |
| Deionized water | ad 100 | ad 100 |
| Polyquaternium-10 (conditioning agent) | 0.10 | 0.10 |
| Pentasodium pentatate (chelating agent) | 0.10 | 0.10 |
| Phosphoric acid (pH adjuster) | q.s. to pH 3 | q.s. to pH 3 |
| Hydrogen peroxide (35% available oxygen) (oxidizing agent) | 2.86 | 5.71 |

The solution of Example 10 (1 percent available oxygen) was compared to a conventional neutralizing solution (2 percent available oxygen) in the following test. Two sets of hair were reduced in this Example. One set of hair was neutralized with a conventional neutralizing solution for 5 minutes and rinsed with water for 5 minutes. The second set of hair had the oxidizing solution of the present invention (Example 10) applied, left on and dried. The tress length was measured and the curl durability determined using the general procedure described in Example 9. The results are as described in Table III below.

TABLE III

| Type of Perm Process | Results | |
| --- | --- | --- |
| Conventional Permanent Waving Process | 1a. Initial dry curl length (cm) when neutralized with conventional neutralizing solution | 11.0 |
| | 1b. Dry curl length (cm) after one shampoo | 13.0 |
| | Durability of Curl (cm) | 2.0 |
| Permanent Waving Process of the Present Invention | 2a. Initial dry curl length (cm) when solution of Example 10 used and left on hair | 10.5 |
| | 2b. Dry curl length (cm) after one shampoo | 12.0 |
| | Durability of Curl (cm) | 1.5 |

EXAMPLE 11

An oxidizing solution formulation was prepared by mixing the following ingredients described in Table IV below.

TABLE IV

| Ingredient | Percent by Weight |
| --- | --- |
| Deionized water (solvent) | ad 100 |
| Phosphoric acid (pH adjuster) | q.s. to pH 3 |
| Pentasodium pentatate (chelator) | 0.10 |
| Sodium perborate (oxidant) (15% available oxygen) | 4.50 |
| Laureth-23 (solubilizer) | 0.10 |
| Fragrance | 0.01 |
| Conditioning agent | 3.50 |

Stability measurements were carried out on the formulation above. The formulation was analyzed via titration to determine stability after periods of 3 months, 6 months and 12 months by measuring percent available oxygen in the formulation. The percent available oxygen in the formulation remained essentially constant at about 1.4 percent during the above periods.

EXAMPLE 12 AND COMPARATIVE EXAMPLE

An oxidizing solution of an embodiment of the present invention was applied to several tresses of hair which had been treated with a mild alkaline-reducing solution. The oxidizing solution was left on the hair and the hair was dried. After the hair was dried, the hair was shampooed five times either (a) immediately, (b) after a 24 hour, or (c) after a 48 hour waiting period. The cress length was measured and the curl durability was determined using the general procedure described in Example 9. The average tress length and average curl durability results for five tresses is shown in Table V below.

TABLE V

| Shampoo Waiting Period | Average Initial Dry Length (cm) | Average Dry Length After 5 Shampoos (cm) | Average Length Difference (cm) |
| --- | --- | --- | --- |
| Shampoo Immediately After Drying Hair | 7.3 | 7.6 | 0.3 |
| Shampoo 24 Hours After Drying Hair | 7.0 | 7.4 | 0.4 |
| Shampoo 48 Hours After Drying Hair | 6.7 | 7.6 | 0.9 |

A solution of conventional neutralizing (comparative example) was prepared and applied to several tresses of hair which had been treated with a mild alkaline-reducing solution. The neutralizing was rinsed off thoroughly and the hair dried. The hair was shampooed five times either (a) immediately, (b) after a 24 hour, or (c) after a 48 hour waiting period. The tress length was measured and the curl durability was determined using the general procedure described in Example 9. The results are shown in Table VI below.

TABLE VI

| Shampoo Waiting Period | Average Initial Dry Length (cm) | Average Dry Length After 5 Shampoos (cm) | Average Length Difference (cm) |
| --- | --- | --- | --- |
| Shampoo Immediately After Drying Hair | 6.3 | 7.2 | 0.9 |
| Shampoo 24 Hours After Drying Hair | 6.1 | 7.5 | 1.4 |
| Shampoo 48 Hours After Drying Hair | 6.0 | 7.5 | 1.5 |

The above data in Tables V and VI show improved curl durability using the oxidizing solution of the present invention over the solution of the comparative example. Additionally, the data above show that shampooing hair immediately after drying is most preferred for maintaining curl in the hair when the oxidizing solution and process of the present invention is used. Shampooing immediately after drying hair which has been permed is contrary to the general knowledge in the prior art which teaches that one must wait at least 24 hours, and preferably 48 hours, before shampooing hair after a permanent wave in order to maintain curl in the hair.

EXAMPLE 13

This example was carried out to evaluate the affect of the solutions of the present invention on color of hair. Medium brown hair of 8 inches length was assembled into eight 2.5 gram tresses. Four of the tresses were treated with a mild alkaline-reducing solution and four of the tresses were left untreated. Each one of the following solutions described in Table VII below was applied to one treated tress and one untreated tress.

TABLE VII

| | Solution (% by weight) | | | |
| --- | --- | --- | --- | --- |
| Ingredient | A | B | C | D |
| Deionized water | ad 100 | ad 100 | ad 100 | ad 100 |
| Pentasodium pentatate | 0.10 | 0.10 | 0.10 | 0.10 |
| Polyquaternium-7 | 1.00 | 1.00 | 1.00 | 1.00 |
| Acetamidopropyl trimonium chloride | 0.50 | 0.50 | 0.50 | 0.50 |
| Laureth-23 | 0.1 | 0.10 | 0.10 | 0.10 |
| Fragrance | 0.01 | 0.01 | 0.01 | 0.01 |
| Phosphoric Acid for adjustment to pH 3 | q.s. | q.s. | q.s. | q.s. |
| Hydrogen peroxide (35% available $O_2$) | 0.00 | 2.86 | 5.71 | 8.57 |

Each tress was then combed and dried followed by exposure to artificial daylight with UV for 24 hours. The tresses were then ranked by seven trained evaluators under controlled conditions from darkest to lightest color. The results are shown in Table VIII below.

TABLE VIII

| | Sample Color Ranking | | | | | | | |
|---|---|---|---|---|---|---|---|---|
| Evaluator | Dark | | | | | | → Light | |
| 1 | VA | VB | PA | PB | PD | PC | VC | VD |
| 2 | VA | VB | PB | PA | PC | PD | VC | VD |
| 3 | VA | VB | PA | PB | VC | PD | PC | VD |
| 4 | VA | VB | PB | PA | VC | PD | PC | VD |
| 5 | VA | VB | PB | PA | PD | PC | VC | VD |
| 6 | VA | VB | PA | PB | VC | PC | PD | VD |
| 7 | VA | VB | PA | PB | PC | VC | PD | VD |

P = Treated with reducing agent
V = Not treated vith reducing agent
A–D = The particular solution of Table VII applied The results of this evaluation clearly show that higher hydrogen peroxide concentrations, specifically 2.0% and 3.0% available oxygen, cause more color fading when left on the hair.

What is claimed is:

1. A process for permanent waving of hair consisting essentially of applying a reducing solution on the hair; applying an aqueous leave-on oxidizing solution on the hair; and drying the hair with the oxidizing solution remaining on the hair.

2. The process of claim 1 wherein the aqueous leave-on oxidizing solution comprises a functional amount of oxidant to provide a concentration of available oxygen in the solution and to provide oxidation of the hair, said oxidant capable of being left on the hair and dried on the hair without damage to the hair; a sufficient amount of an acidic agent to adjust the pH of the oxidizing solution to a pH of less than 7; and water.

3. A process for permanent waving of hair consisting essentially of the steps of:
   (a) wrapping the hair on a means for providing the hair with mechanical tension;
   (b) applying a reducing solution on the hair;
   (c) rinsing off the reducing solution from the hair;
   (d) applying an oxidizing solution to the hair; and
   (e) drying the hair with the oxidizing solution remaining on the hair.

4. The process of claim 3 including removing the mechanical tensioning means from the hair prior to applying the oxidizing solution to the hair.

5. The process of claim 3 including removing the mechanical tensioning means from the hair after applying the oxidizing solution to the hair.

6. The process of claim 3, wherein the step of applying an oxidizing solution to the hair includes applying an the aqueous leave-on oxidizing solution, the oxidizing solution including a functional amount of oxidant to provide concentration of available oxygen in this solution and to provide oxidation of the hair, a sufficient amount of acidic agent to adjust the pH of the oxidizing solution to a pH of less than 7; and water; wherein the concentration of available oxygen is in the range of from about 0.5 to about 2.0 weight percent, the pH of the oxidizing solution is in the range from about 2 to about 6 and the oxidant is an oxygen donor.

7. The process of claim 6, wherein the oxidant is an alkali metal perborate.

8. A process for permanently waving hair, the process consisting essentially of (1) applying a reducing solution to the hair; (2) applying an aqueous leave-on oxidizing solution on the hair; and (3) drying the hair with the oxidizing solution remaining on the hair; wherein the aqueous leave-on oxidizing solution includes a functional amount of oxidant to provide concentration of available oxygen in this solution and to provide oxidation of the hair, a sufficient amount of acidic agent to adjust the pH of the oxidizing solution to a pH of less than 7; and water; wherein the concentration of available oxygen is in the range of from about 0.5 to about 2.0 weight percent, the pH of the oxidizing solution is in the range from about 2 to about 6 and the oxidant is an oxygen donor.

9. The process of claim 8, wherein the oxidant is an alkali metal perborate.

* * * * *